United States Patent [19]

Robbins

[11] Patent Number: 4,605,522

[45] Date of Patent: Aug. 12, 1986

[54] METHOD FOR PREPARATION OF N-PHOSPHONOMETHYLGLYCINE OR SALTS

[75] Inventor: Jeffery D. Robbins, Berkeley, Calif.

[73] Assignee: Stauffer Chemical Company, Westport, Conn.

[21] Appl. No.: 672,323

[22] Filed: Nov. 19, 1984

Related U.S. Application Data

[63] Continuation-in-part of Ser. No. 499,017, May 17, 1983, abandoned.

[51] Int. Cl.$^4$ ............................................... C07F 9/38
[52] U.S. Cl. ............................................... 260/502.5 F
[58] Field of Search ................................. 260/502.5 F

[56] References Cited

U.S. PATENT DOCUMENTS

| | | | |
|---|---|---|---|
| 3,052,362 | 12/1974 | Lambert | 260/502.4 R |
| 3,160,632 | 12/1964 | Toy et al. | 260/502.5 E |
| 3,799,758 | 3/1974 | Franz | 260/501.12 |
| 4,331,591 | 5/1982 | Baylis | 260/502.5 E |
| 4,442,041 | 4/1984 | Subramanian | 260/502.5 F |

OTHER PUBLICATIONS

Uhing et al., "J. Am. Chem. Soc.", vol. 83 (1961), pp. 2299–2303.

*Primary Examiner*—J. E. Evans
*Attorney, Agent, or Firm*—Paul R. Martin

[57] ABSTRACT

A method for the production of N-phosphonomethylglycine and soluble salts thereof is disclosed in which glycinemethylenephosphinic acid or its soluble salts are reacted with an excess of an alkali or alkaline earth base for a period of time and at a sufficient temperature to cause oxidation of the glycinemethylenephosphinic acid or its soluble salts thereof to N-phosphonomethylglycine salts, from which N-phosphonomethylglycine may be obtained by acidification. The N-phosphonomethyleglycine or its soluble salts, are used as herbicides.

5 Claims, No Drawings

METHOD FOR PREPARATION OF N-PHOSPHONOMETHYLGLYCINE OR SALTS

CROSS REFERENCE TO RELATED APPLICATIONS

This application is a continuation-in-part of application Ser. No. 499,017, filed May 27, 1983 now abandoned.

BACKGROUND OF THE INVENTION

This invention relates to a novel method for the preparation of N-phosphonomethylglycine or salts thereof, a compound which is a known herbicide and plant growth regulator.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way. There are a number of different types of herbicides presently sold commercially, and these fall into two general categories. The categories are pre-emergence and postemergence herbicides. The pre-emergence herbicides are applied to the soil prior to the emergence of the weed plants from the soil, and the post-emergence herbicides are applied to plant surfaces after emergence of the weeds or other unwanted plants from the soil.

One of the earliest post-emergence herbicides used commercially was 2,4-D (2,4-dichlorophenoxyacetic acid). After a number of years of use of this and similar compounds such as 2,4,5-T (2,4,5-trichlorophenoxy acetic acid), it was found that certain decomposition products of these herbicides were long lasting and were not biodegradable. While there has been some dispute between governmental agencies and commercial interests regarding the effects of residual products of 2,4-D, 2,4,5-T and similar compounds, the agencies nevertheless restricted the use of these herbicides in the United States some years ago. Since that time, efforts have been made to develop herbicides which are biodegradable into harmless residues within a relatively short time after their application.

One such compound, which has been found to be biodegradable, yet which is effective as a herbicide and plant growth regulator when employed at lower rates, is N-phosphonomethylglycine and various salts thereof. The N-phosphonomethylglycine and agriculturally effective salts have been approved for use by the U.S. government, and, as a consequence, this herbicide has become extremely successful commercially.

N-Phosphonomethylglycine and certain salts are the only effective and approved post-emergence herbicides in the field. The present commercial compound is the isopropylamine salt of N-phosphonomethylglycine and derivatives thereof.

In field use it is normally applied in amounts of from 0.01 to about 20 pounds per acre, preferably from 2 to 6 pounds per acre.

N-Phosphonomethylglycines, and certain soluble salts thereof, can be made in a number of different ways. One such method, as described in U.S. Pat. No. 3,160,632 (Toy et al., Dec. 8, 1964) is to react N-phosphinomethylglycine (glycinemethylenephosphinic acid) with mercuric chloride in a water solvent at reflux temperature, and subsequently separating the reaction products. Another method involves the reaction of ethyl glycinate with formaldehyde and diethylphosphite and subsequent hydrolysis. The latter method is described in U.S. Pat. No. 3,799,758 (Franz, Mar. 26, 1974). In addition, there is a whole series of patents, relating to N-phosphonomethylglycine, its salts, and derivatives thereof, described as being useful herbicides and plant growth regulators. Such additional patents relating to N-phosphonomethylglycine, methods of application, methods of preparation, salts, and derivatives, include U.S. Pat. Nos. 3,868,407, 4,197,254, and 4,199,354, among others.

Because of the importance of N-phosphonomethylglycine and certain salts as a herbicide, other methods of making the compounds are constantly being sought in order to provide improved or alternate methods of manufacture.

SUMMARY OF THE INVENTION

It has now been discovered that N-phosphonomethylglycine or soluble salts thereof, can be produced in good yields by the oxidation of glycinemethylenephosphinic acid or salts thereof with an alkali or alkaline earth metal base, the preferred one being concentrated aqueous sodium hydroxide. The formula for this reaction (using sodium hydroxide as the base) can be represented as follows:

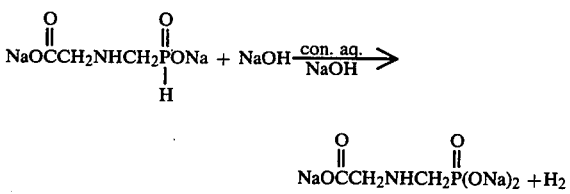

The reaction is preferably carried out in a conventional reaction vessel under such conditions of temperature and pressure so as to obtain maximum yield. Preferably, the temperature ranges from about 110° to about 150° C., and most preferably from about 125° to 135° C. The reaction is normally carried out at atmospheric pressure, although if increased pressure is used, the reaction time will be diminished.

The time of the reaction will vary depending on the temperature used, but in general will range from about 2 to about 12 hours.

While sodium hydroxide is the base of choice, other suitable bases include lithium hydroxide, cesium hydroxide, potassium hydroxide, barium hydroxide, and calcium oxide.

The reaction is preferably conducted in an excess of aqueous sodium hydroxide or other base, the excess of aqueous sodium hydroxide serving as the reaction medium.

The mole ratio of glycinemethylenephosphinic acid or soluble salt starting material to the preferred base, sodium hydroxide, can range from about 0.02 to about 0.5, with the preferred ratio being 0.10 moles of glycinemethylene phosphinic acid to 1 mole of sodium hydroxide. Most preferably, there is present in the reaction solution from about 10 to about 37 moles of NaOH per mole of glycinemethylene phosphinic acid, or disodium salt thereof. As previously indicated, an excess of sodium hydroxide or other base is normally used in order to provide a reaction medium for the reactants.

The glycinemethylenephosphinic acid can be prepared by the method described in U.S. Pat. No. 3,160,632.

This invention will be better understood by reference to the specific examples which follow, which are presented as merely illustrative, non-limiting demonstrations of the method of the instant invention.

EXAMPLE 1

Preparation of Sodium Salt of N-Phosphonomethylglycine

A three-necked, 50 milliliter (ml) round-bottom flask is equipped with a magnetic stirrer, a nitrogen bubbler, a reflux condenser, and a thermometer situated in a heating mantle. To this flask was added 1.5 grams (g) (7.7 mmole) of 79 wt. % pure glycinemethylenephosphinic acid, and 15 ml (ca 287 mmol) of 50% sodium hdyroxide. The ingredients were combined under a nitrogen atmosphere, and the reaction mixture was then heated to reflux temperature. The reactants were refluxed for approximately 120 minutes at a temperature of approximately 128° C. Thereafter, the solution was cooled under nitrogen, weighed and quantitatively analyzed by high performance liquid chromatography (hplc) and a strong anion exchange column. The yield of the trisodium salt of N-phosphonomethylglycine was 65% of theory. The presence of this salt was confirmed by $^{13}$C nmr spectroscopy.

EXAMPLE 2

Preparation of Sodium Salt of N-Phosphonomethylglycine

A 50 ml three-necked round-bottom flask was equipped with a heating mantle, a stirring bar, a thermometer, and a reflux condenser with a nitrogen bubbler. To this flask was added 9.8 g (122 mmol) of 50% sodium hydroxide and 20 g of an aqueous solution that contained 12.2 mmole of glycinemethylenephosphinic acid disodium salt. The solution was heated to reflux temperature, which was approximately 106° C., and refluxed for approximately 3 hours. Hplc analysis indicated that the reaction was very sluggish at this temperature. The apparatus was modified for distillation and water was distilled until the temperature of the reaction mixture reached 130° C. The mixture was maintained at this temperature for 8.0 hours and then cooled. The cooled reaction mixture was analyzed quantitatively by hplc and found to contain 7.3 mmole (60% of theory) of the trisodium salt of N-phosphonomethylglycine. Crystalline N-phosphonomethylglycine (4.4 mmol, 36% yield) was obtained from the reaction mixture by acidification to pH 1.4, chilling and seeding.

The N-phosphonomethylglycine acid compound which is produced in accordance with the method of the invention, in and of itself, has herbicidal and plant growth regulating efficacy. However, because the free acid is not in itself very soluble in aqueous solutions, it is preferred to convert the compound to salt form for inclusion into herbicidal compositions. Salt forms which have been found to have high rates of herbicidal activity and plant growth regulating activity are the trialkylsulfonium salts, such as are disclosed in U.S. Pat. No. 4,315,765.

It will be appreciated by those skilled in the art that variations in times, temperatures, pressures, and the like can be had in the method of the invention without departing from the spirit of the invention and the scope of the claims herein.

What is claimed is:

1. A method for the production of N-phosphonomethylglycine and soluble salts thereof which comprises reacting glycinemethylenephosphinic acid or soluble salts thereof with an excess of an alkali or alkaline earth base for a period of time and at a temperature ranging from about 125° C. to about 135° C., sufficient to cause oxidation of the glycinemethylenephosphinic acid or soluble salts thereof to N-phosphonomethylglycine salts, wherein there is present in solution an amount of alkali or alkaline earth base equivalent to from about 10 to about 37 moles of sodium hydroxide per mole of glycinemethylene phosphinic acid or disodium salt thereof.

2. The method of claim 1 in which said base is concentrated aqueous sodium hydroxide.

3. The method of claim 1 in which the reaction is carried out at atmospheric pressure.

4. The method of claim 1 in which base is selected from the group consisting of sodium hydroxide, potassium hydroxide, lithium hydroxide, cesium hydroxide, barium hydroxide and calcium oxide.

5. The method of claim 1 in which the product is acidified to form N-phosphonomethylglycine.

* * * * *